US006716579B1

(12) United States Patent
Baidya et al.

(10) Patent No.: US 6,716,579 B1
(45) Date of Patent: Apr. 6, 2004

(54) GENE SPECIFIC ARRAYS, PREPARATION AND USE

(76) Inventors: Narayan Baidya, 398 Boynton Ave., #10, San Jose, CA (US) 95117; Yii-Der Ida Chen, 21871 Via Regina, Saratoga, CA (US) 95070; Julie Holding, 3555 La Manta Way, Palo Alto, CA (US) 94306; Yie-Teh Yu, 1045 Santa Cruz Ave., #C., Menlo Park, CA (US) 94025

( * ) Notice: Subject to any disclaimer, the term of this patent is extended or adjusted under 35 U.S.C. 154(b) by 0 days.

(21) Appl. No.: 09/591,366

(22) Filed: Jun. 9, 2000

Related U.S. Application Data
(60) Provisional application No. 60/138,690, filed on Jun. 11, 1999.

(51) Int. Cl.⁷ .......................... C12Q 1/68; G01N 15/00; C07H 21/00
(52) U.S. Cl. .................. 435/6; 422/68.1; 536/23.1
(58) Field of Search .............. 435/6, 69.1; 536/23.1; 422/68.1; 702/20

(56) References Cited

U.S. PATENT DOCUMENTS

| | | | |
|---|---|---|---|
| 5,143,854 A | | 9/1992 | Pirrung et al. ............ 436/518 |
| 5,510,270 A | * | 4/1996 | Fodor et al. ............. 436/518 |
| 5,800,992 A | | 9/1998 | Fodor et al. ............... 435/6 |
| 5,807,522 A | | 9/1998 | Brown et al. ............. 422/50 |
| 5,837,832 A | | 11/1998 | Chee et al. .............. 536/22.1 |

FOREIGN PATENT DOCUMENTS

| | | |
|---|---|---|
| WO | WO 92/10092 | 6/1992 |
| WO | WO 93/09668 | 5/1993 |
| WO | WO 97/10365 | 3/1997 |
| WO | WO 98/53103 | 11/1998 |
| WO | WO 99/05323 A1 | 2/1999 |

OTHER PUBLICATIONS

Genbank Accession No. U36596, 1995.*
Genbank Accession No. J04185, 1998.*
Genbank Accession No. Z18205, 1992.*
Genbank Accession No. H 36236, 1997.*
Genbank Accession No. U 36594, 1995.*
Genbank Accession No. T45783, 1998.*
Genbank Accession No. U36595, 1995.*
Genbank Accession No. T04477, 1998.*
Genbank Accession No. R 87034, 1998.*
Genbank Accession No. T 14152, 1998.*
Genbank Accession No. T22720, 1997.*
Wilcox et al., Nucleic Acids Research, vol. 19, No. 8, pp. 1837–1843, 1991.*
Research Genetics Brochure "Gene Filters™. Thousands of Genes on a Single Membrane: Human GeneFilters™," Research Genetics: Huntsville, AL., 4 pages, (or see web site visited Aug. 15, 2000 www.resgen.com.

Chen, J.J. et al. (1998). "Profiling Expression Patterns and Isolating Differentially Expressed Genes by cDNA Microarray System with Colorimetry Detection," *Genomics* 51:313–324.

Duggan, D.J. et al. (Jan. 1999). "Expression Profiling Using cDNA Microarrays," *Nat. Genetics* 21(Suppl.):10–14.

Guyer, M.S. and Collins, F.S. (Nov. 1995). "How is the Human Genome Project Doing, and What Have We Learned So Far?" *Proc. Natl. Acad. Sci. USA* 92:10841–10848.

Heller, R.A. et al. (Mar. 1997). "Discovery and Analysis of Inflammatory Disease–Related Genes Using cDNA Microarrays," *Proc. Natl. Acad. Sci USA* 94:2150–2155.

Karlin, S. and Altschul, S.F. (Mar. 1990). "Methods for Assessing the Statistical Significance of Molecular Sequence Features by Using General Scoring Schemes," *Proc. Natl. Acad. Sci. USA* 87:2264–2268.

Khan, J. et al. (Feb. 1999). "Expression Profiling in Cancer Using cDNA Microarrays," *Electrophoresis* 20:223–229.

Khrapko, K.R. et al. (Oct. 1989). "An Oligonucleotide Hybridization Approach to DNA Sequencing," *FEBS Letts.* 256(1–2):118–122.

Lennon, G. et al., (Feb. 1996). "The I.M.A.G.E. Consortium: An Integrated Molecular Analysis of Genomes and Their Expression," *Genomics* 33:151–152.

Liang, P. and Pardee, A.B. (Aug. 14, 1992). "Differential Display of Eukaryotic Messenger RNA by Means of the Polymerase Chain Reaction," *Science* 257:967–971.

Rowen, L. et al. (Oct. 24, 1997). "Sequencing the Human Genome," *Science* 278:605–607.

Schena, M. et al. (Oct. 1996). "Parallel Human Genome Analysis: Microarray–Based Expression Monitoring of 1000 Genes," *Proc. Natl. Acad. Sci USA* 93:10614–10619.

Schuler, G.D. et al. (Oct. 25, 1996). "A Gene Map of the Human Genome," *Science* 274:540–546.

Schuler, G.D. (1997). "Pieces of the puzzle: expressed sequence tags and the catalog of human genes" *J. Mol. Med.* 75(10):694–698.

Wang, K. et al. (1999). "Monitoring Gene Expression Profile Changes in Ovarian Carcinomas Using cDNA Microarray," *Gene* 229:101–108.

(List continued on next page.)

*Primary Examiner*—Ardin H. Marschel
(74) *Attorney, Agent, or Firm*—Clingenix, Inc.

(57) ABSTRACT

The present invention provides arrays comprising a plurality of polynucleotide probes having sequences complementary to the 3' untranslated region of a gene transcript, whose chromosomal location has been defined. The arrays are particularly useful for conducting comparative gene expression analyses. The present invention also includes a method of preparing these arrays and various methods of using these arrays for detecting differential expression of multiple gene transcripts amongst multiple subjects. Further provided by the invention are computer readable media recorded thereon an array of polynucleotide probes as specified herein, a computer-based system, and kits for detecting differential expression of a multiplicity of gene transcripts.

24 Claims, No Drawings

OTHER PUBLICATIONS

Wood, W.I. et al. (Mar. 1985). "Base Composition–Independent Hybridization in Tetramethylammonium Chloride: A Method for Oligonucleotide Screening of Highly Complex Gene Libraries," *Proc. Natl. Acad. Sci. USA* 82:1585–1588.

Basett, D. et al. (1999). "Gene Expression Informatics—It's all in your mine," Nature Genetics 21: 51–55.

Bowtell, D.L. (1999). "Options Available—From Start to Finish—For Obtaining Expression Data by Microarray," *Nature Genetics Supplement* 21:25–32.

Ermolaeva, O. et al. (1998). "Data Management and Analysis for Gene Expression Arrays," *Nature Genetics* 20:19–23.

Schena, M. et al. (1995). "Quantitative Monitoring of Gene Expression Patterns with a Complementary DNA Microarray," *Science, U.S. American Association for the Advancement of Science* 270(5235): 467–470.

\* cited by examiner

GENE SPECIFIC ARRAYS, PREPARATION AND USE

CROSS-REFERENCE TO RELATED APPLICATIONS

This application claims the priority benefit of U.S. Provisional Application No. 60/138,690, filed Jun. 11, 1999, which is incorporated herein by reference.

TECHNICAL FIELD

This invention is in the field of genetic analysis. Specifically, the invention relates to the generation of an array of polynucleotide probes comprising sequences complementary to the 3' untranslated region of a gene transcript, whose chromosomal location has been defined. The compositions and methods embodied in the present invention are particularly useful for high throughput screening of differential gene expression patterns among multiple subjects.

BACKGROUND OF THE INVENTION

The structure and biological behavior of a cell is determined by the pattern of gene expression within that cell. Each human cell contains approximately three billion base pairs encoding between 50,000 to 100,000 genes (Schuler et al. (1996) *Science* 274:540–546; Guyer et al. (1995) *Proc. Natl. Acad. Scie.* USA 92:10841–10848; Rowen et al. (1997) *Science* 278:605–607). In any given cell only a fraction of these genes is being actively transcribed. Deciphering the fundamental structure and biological behavior of any given cell requires knowledge of which genes are transcribed and the relative abundance of those transcribed genes.

Perturbations of gene expression have long been acknowledged to account for a vast number of diseases including, numerous forms of cancer, vascular diseases, neuronal and endocrine diseases. Abnormal expression patterns, in form of amplification, deletion, gene rearrangements, and loss or gain of function mutations, are now known to lead to aberrant behavior of a disease cell. In the case of cancer, a deviated expression profile from that of a normal progenitor cell may result in dysfunction of cellular processes, which ultimately lead to dysregulated growth, lack of anchorage inhibition, genomic instability and propensity for cell metastasis.

Monitoring the expression profile of a panel of genes to determine the role of genes in regulating any cellular process has until now been a daunting task. Traditional approaches for identifying transcripts unique to a particular cell type are generally highly focused, targeting only one specific gene or chromosome region at a time. Conventional techniques such as cDNA subtraction, differential display (Liang et al. (1992) *Science* 257:967–971), expressed sequence tag (EST) isolation, provide valuable tools for comparative gene expression analysis, but they have pronounced limitations. Whereas these approaches to certain extent yield quantitative information about the abundance of the gene transcripts of particular interest, they do not provide insight systematically into global gene expression patterns. Recently, a new technique, array-based analysis has emerged in the study of genome-wide expression.

The array-based technology involves hybridization of a pool of target polynucleotides corresponding to gene transcripts of a test subject to an array of tens and thousands of probe sequences immobilized on the array substrate. The technique allows simultaneous detection of multiple gene transcripts and yields quantitative information on the relative abundance of each gene transcript expressed in a test subject. By comparing the hybridization patterns generated by hybridizing different pools of target polynucleotides to the arrays, one can readily obtain the relative transcript abundance in two pools of target samples. The analysis can be extended to detecting differential expression of genes between diseased and normal tissues, among different types of tissues and cells, amongst cells at different cell-cycle points or at different developmental stages, and amongst cells that are subjected to various environmental stimuli or lead drugs.

Currently employed arrays including oligonucleotide arrays and cDNA arrays bear a number of intrinsic limitations. WO 97/10365 describes an oligonucleotide array made of synthetically generated oligonucleotides of 20–500 nucleotides in length; each of the following references WO 98/53103, Duggan et al. (1999) *Nature Genetics Supplement* 21: 10–14, Wang et al. (1999) *Gene* 229: 101–108, Khan et al. (1999) *Electrophoresis* 20: 223–229, and Chen et al. (1998) *Genomics* 51: 313–324, describes a DNA microarray for monitoring changes in gene expression profile of one or multiple test subjects. Neither of these references discloses arrays necessarily contains probes having minimum secondary structure and lacking internal sequence homology. These are necessary criteria for achieving optimal hybridization efficiency and signal/noise ratio. The wide range of oligonucleotide length (20–500 bases as disclosed in WO 97/10365, 120–1000 bases as specified in WO 98/53103), and hence the thermal stability profile of the probes, inevitably introduces intrinsic variability to the hybridization efficiency of the arrays. There thus remains a considerable need for arrays of probes that are more uniform, highly specific, and more applicable for genome-wide study of expression patterns.

SUMMARY OF THE INVENTION

A principal aspect of the present invention is the design of arrays of polynucleotide probes having reduced secondary structures. Such arrays are highly specific for simultaneous detection of differential expression of multiple genes. Accordingly, the present invention provides an array comprising a plurality of polynucleotide probes immobilized on a solid support, which exhibits the following characteristics: (a) the plurality of polynucleotide probes corresponds to a multiplicity of gene transcripts; (b) each polynucleotide probe of the plurality is localized to a predetermined region on a solid support; (c) each polynucleotide probe is from about 50 to about 500 nucleotides in length; and (d) each polynucleotide probe is complementary to 3' untranslated sequence of a gene transcript, said untranslated sequence having a defined chromosomal location.

In one aspect of this embodiment, the arrays of the present invention further comprise control probes which can be normalization control probes, expression level control probes, and/or mismatch control probes. In another aspect, the arrays comprise target polynucleotides corresponding to gene transcripts expressed in a subject, wherein the target polynucleotides are bound to the polynucleotide probes in form of stable target-probe complexes.

In a separate aspect, the plurality of polynucleotide probes immobilized on the arrays may comprise at least about 10 polynucleotides, each being complementary to a distinct gene transcript. Preferably, the plurality of polynucleotide probes comprises at least about 100 polynucleotides. In a preferred embodiment, an array comprises a plurality of sequence-tagged site (STS) tags.

In yet another separate aspect, the predetermined region of the invention array comprises at least 10 single-stranded polynucleotides that are complementary to the same gene transcript. The predetermined region may also comprise at least 100 single-stranded polynucleotides that are complementary to the same gene transcript. In a preferred embodiment, the predetermined region comprises single-stranded polynucleotides of identical sequences.

The solid support on which the probes are arrayed can be flexible or rigid. Preferably, the solid support is made of one or more substances selected from the group consisting of nitrocellulose, nylon, polypropylene, glass, and silicon.

The present invention also provides a method of preparing and using an array having the above-mentioned characteristics.

In one embodiment, the present invention provides a method of simultaneously detecting expression of a multiplicity of gene transcripts of a subject. The method comprises the steps of: (a) contacting more than one labeled target polynucleotides corresponding to gene transcripts of said subject with an array of polynucleotide probes as disclosed herein under the conditions sufficient to produce stable target-probe complexes; and (b) detecting the formation of the stable target-probe complexes, thereby detecting expression of a multiplicity of gene transcripts.

In another embodiment, the invention provides a method of detecting differential expression of a multiplicity of gene transcripts of at least two subjects. The method involves (a) contacting more than one labeled target polynucleotides corresponding to gene transcripts of a first subject with an invention array, under the conditions sufficient to produce stable target-probe complexes that form a first hybridization pattern; (b) contacting more than one labeled target polynucleotides corresponding to gene transcripts of a second subject with an invention array, under the conditions sufficient to produce stable target-probe complexes that form a second hybridization pattern; and (c) comparing the hybridization patterns, thereby detecting the differential expression of a multiplicity of gene transcripts of the subjects. In one aspect of this embodiment, the hybridization patterns are generated on the same array. In another aspect of the embodiment, the hybridization patterns are generated on different arrays. The target polynucleotides can be DNA or RNA molecules, and preferably cDNAs.

The present invention also includes a computer readable medium having recorded thereon arrays of polynucleotide probes as disclosed herein. Featured computer media include magnetic storage medium, optical storage medium, electrical storage medium, hybrid storage medium of any of these categories.

The invention further provides a computer-based system for detecting differential expression of a multiplicity of gene transcripts indicated by a difference in hybridization patterns on an array of polynucleotide probes. The computer-based system comprises: a) a data storage device comprising a reference hybridization pattern and a test hybridization pattern, wherein the reference hybridization pattern is generated by hybridizing an array of polynucleotide probes having the above-described characteristics, with more than one labeled target polynucleotides corresponding to gene transcripts expressed in a control; and wherein the test hybridization pattern is generated by hybridizing an invention array of polynucleotide probes with more than one labeled target polynucleotides corresponding to gene transcripts expressed in a test subject; b) a search device for comparing the test hybridization pattern to the reference hybridization pattern of the data storage device of step (a) to detect the differences in hybridization patterns; and c) a retrieval device for obtaining said differences in hybridization patterns of step (b).

Also embodied in the invention is a method of determining differential expression of a multiplicity of gene transcripts of at least two subjects using a computer.

Further provided by the invention are kits containing the invention arrays for simultaneous detection of expression of multiple gene transcripts.

MODE(S) FOR CARRYING OUT THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The terms "polynucleotide", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component A "polynucleotide probe" refers to a polynucleotide used for detecting or identifying its corresponding target polynucleotide in a hybridization reaction.

A "gene" refers to a polynucleotide containing at least one open reading frame that is capable of encoding a particular protein after being transcribed and translated.

The phrase "3' untranslated sequences" as applied to a gene transcript refers to the 3' end sequences located immediately outside the open reading frame of the gene transcript. The part of 3' untranslated sequences that has a defined chromosomal location excludes the poly-A tail located at the very end of the 3' untranslated region.

"Genes of a specific developmental origin" refer to genes expressed at certain but not all developmental stages. For instance, a gene may be of embryonic or adult origin depending on the stage during which the gene is expressed.

A disease-associated gene refers to any gene which is yielding transcription or translation products at an abnormal level or in an abnormal form in cells derived from a disease-affected tissues compared with tissues or cells of a control. It may be a gene that becomes expressed at an abnormally high level; it may be a gene that becomes expressed at an abnormally low level, where the altered expression correlates with the occurrence and/or progression of the disease. A disease-associated gene also refers to gene possessing mutation(s) or genetic variation that is directly responsible or is in linkage disequilibrium with gene(s) that is responsible for the etiology of a disease. The transcribed or translated products may be known or unknown, and may be at normal or abnormal level.

Different polynucleotides are said to "correspond" to each other if one is ultimately derived from another. For example, a sense strand corresponds to the anti-sense strand of the same double-stranded sequence. mRNA (also known as gene transcript) corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. Polynucleotides may be said to correspond even when one of the pair is derived from only a portion of the other.

A gene "database" denotes a set of stored data which represent a collection of sequences including nucleotide and peptide sequences, which in turn represent a collection of biological reference materials.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as gene product. If the polynucleotide is derived from genomic DNA, expression may include splicing of the mRNA in an eukaryotic cell.

"Differentially expressed", as applied to nucleotide sequence or polypeptide sequence in a subject, refers to over-expression or under-expression of that sequence when compared to that detected in a control. Underexpression also encompass absence of expression of a particular sequence as evidenced by the absence of detectable expression of in a test subject when compared to a control.

"Differential expression" refers to alterations in the abundance or the expression pattern of a gene product. An alteration in "expression pattern" may be indicated by a change in sub-tissue distribution, or a change in hybridization pattern reviewed on an array of the present invention.

A "primer" is a short polynucleotide, generally with a free 3'-OH group, that binds to a target or "template" potentially present in a sample of interest by hybridizing with the target, and thereafter promoting polymerization of a polynucleotide complementary to the target.

The term "hybridize" as applied to a polynucleotide refers to the ability of the polynucleotide to form a complex that is stabilized via hydrogen bonding between the bases of the nucleotide residues in a hybridization reaction. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

Hybridization can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

"Luminescence" is the term commonly used to refer to the emission of light from a substance for any reason other than a rise in its temperature. In general, atoms or molecules emit photons of electromagnetic energy (e.g., light) when then move from an "excited state" to a lower energy state (usually the ground state); this process is often referred to as "radiative decay". There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" of the present invention may have any one of the above-described properties.

A "predefined region" as used herein refers to a localized area on the surface of a solid support, which is intended for registration or tracking the identify of the polynucleotide probes that are immobilized onto the predefined region.

A "subject" as used herein refers to a biological entity containing expressed genetic materials. The biological entity is preferably a vertebrate, preferably a mammal, more preferably a human. Tissues, cells and their progeny of a biological entity obtained in vivo or cultured in vitro are also encompassed.

A "control" is an alternative subject or sample used in an experiment for comparison purpose. A control can be "positive" or "negative". For example, where the purpose of the experiment is to detect a differentially expressed transcript or polypeptide in cell or tissue affected by a disease of concern, it is generally preferable to use a positive control (a subject or a sample from a subject, exhibiting such differential expression and syndromes characteristic of that disease), and a negative control (a subject or a sample from a subject lacking the differential expression and clinical syndrome of that disease).

Preparation of Arrays

Selection of Probes:

A central aspect of the present invention is the design of an array of polynucleotide probes applicable for detecting differential expression of a multiplicity of genes. Distinguished from the previously described cDNA or oligonucleotide microarrays, the subject arrays have the following unique characteristics: (a) the plurality of polynucleotide probes constituting the array corresponds to a multiplicity of gene transcripts; (b) each polynucleotide probe of the plurality is localized to a predetermined region on a solid support; (c) each polynucleotide probe is from about 50 to about 500 nucleotides in length; (d) each polynucleotide probe is complementary to 3' untranslated sequence of a gene transcript, said untranslated sequence having a defined chromosomal location. A preferred array comprises sequence-tagged site (STS) probes whose chromosomal locations have been identified.

Several factors apply to the design of arrays having the above-mentioned characteristics. First, a selected probe is specific to an expressed gene transcript, and unique to the entire expressed genome. Such unique probe lacks substantial sequence homology with any other existing gene transcripts when optimally aligned, and thus having a low probability of cross-hybridizing with sequences found in any other genes. In general, the 3' untranslated sequence of a gene transcript is highly specific; it typically exhibits little sequence similarity to other expressed genes.

Sequence alignment and homology searches are often determined with the aid of computer methods. A variety of software programs are available in the art. Non-limiting examples of these programs are Blast (available on the worldwide web at http://www. followed by ncbi.nlm.nih.gov/BLAST/), Fasta (Genetics Computing Group package, Madison, Wis.), DNA Star, MegAlign, and GeneJocky. Any sequence databases that contains DNA sequences corresponding to a gene or a segment thereof can be used for sequence analysis. Commonly employed databases include but are not limited to GenBank, EMBL, DDBJ, PDB, SWISS-PROT, EST, STS, GSS, and HTGS. Sequence similarity can be discerned by aligning the probe sequence against a DNA sequence database. Common parameters for determining the extent of homology set forth by one or more of the aforementioned alignment programs include p value and percent sequence identity. P value is the probability that the alignment is produced by chance. For a single alignment, the p value can be calculated according to Karlin et al. (1990) *Proc. Natl. Acad. Sci* 87: 2246. For multiple alignments, the p value can be calculated using a heuristic approach such as the one programmed in Blast. Percent sequence identify is defined by the ratio of the number of nucleotide matches between the query sequence and the known sequence when the two are optimally aligned. A probe sequence is considered to have no substantial homology when the region of alignment exhibits less than 20% of sequence identity, more preferably less than 10% identity, even more preferably less than 5% identity using Fasta alignment program with the default settings.

A second consideration of designing the subject array is to select probes which have minimal secondary structures and internal sequence homology. Extensive homology within the probe due to e.g., inverted repeats, promotes self-hybridization, and thus interfering the binding of the probe to the target sequences.

A further consideration is to choose probes having similar thermal profiles and internal stability. This can be achieved by selecting probes with comparable length and G/C content. Preferably, probes have 50 to 60% G+C composition. Preferably, probes to be arrayed have a minimal length of about 50 nucleotides, more preferably about 100 nucleotide, and even more preferably about 150. Preferably, probes of the subject arrays have a maximal length of about 500 nucleotides, more preferably about 400 nucleotides, and even more preferably about 300 nucleotides. In a preferred embodiment, the probes are generated by amplifying genomic DNA using primers complementary to the 3' untranslated regions of genes of particular interest.

Whereas the arrays of selected probes must correspond to a multiplicity of gene transcripts expressed in a test subject, the types of arrays embodied in the present invention may differ in the nature of the polynucleotide probes immobilized thereon, and specifically the types of genes to which the probes correspond. The types of genes may be characterized based on one or more of the following features: species origin, developmental origin, primary structural similarity, involvement in a particular biological process, association with a particular disease or disease stage, tissue, sub-tissue or cell-specific expression pattern, and subcellular location of the expressed gene product.

In one aspect, the arrays of the present invention comprise probes corresponding to gene transcripts expressed in a eukaryote cell, such as a cell derived from a vertebrate, preferably a mammal, more preferably a primate, even more preferably a human being. In another aspect, the arrays contain probes capable of hybridizing to genes of a specific developmental origin, such as those expressed in an embryo or an adult, during ectoderm, endoderm or mesoderm formation in a multi-cellular organism. In yet another aspect, the invention arrays comprise probes binding to a family of gene transcripts, or a sub-family of gene transcripts that share primary structural similarities. Structural similarities can be discerned with the aid of computer software described above. Non-limiting examples of gene families include those encoding cell surface receptors, protein kinases (e.g. tyrosine, serine/threonine or histidine kinases), trimeric G-proteins, cytokines, SH2-, SH3-, PH-, PDZ-domain containing proteins, and any of those gene families published by Human Genome Sciences Inc., Celera, the Institute for Genomic Research (TIGR), and Incyte Pharmaceuticals, Inc.

In yet another aspect, the arrays present probes recognizing gene transcripts involved in a specific biological process, including but not limited to cell cycle regulation, cell differentiation, apoptosis, chemotaxsis, cell motility and cytoskeletal rearrangement. In still another aspect, the invention arrays contain probes hybridizing to gene transcripts that are associated with a particular disease or with a specific disease stage. Such genes include but are not limited to those associated with autoimmune diseases, obesity, hypertension, diabetes, neuronal and/or muscular degenerative diseases, cardiac diseases, endocrine disorders, any combinations thereof. In yet still another aspect, the arrays of the present invention comprise probes hybridizing to gene transcripts with restricted expression patterns. Non-limiting exemplary gene transcripts of this class include those that are not ubiquitously expressed, but rather are differentially expressed in one or more of the body tissues including heart, liver, prostate, lung, kidney, bone marrow, blood, skin, bladder, brain, muscles, nerves, and selected tissues that are affected by various types of cancer (malignant or non-metastatic), affected by cystic fibrosis or polycystic kidney disease. Additional examples of non-ubiquitously expressed genes are those whose gene products are localized to certain subcellular locations: extracellular matrix, nucleus, cytoplasm, cytoskeleton, plasma and/or intracellular membranous structures which include but are not limited to coated pits, Golgi apparatus, endoplasmic reticulum, endosome, lysosome, and mitochondria A preferred array comprises 3' untranslated sequences of gene transcripts listed in Table 1.

Where desired, the arrays of the present invention comprise control probes, positive or negative, for comparison purpose. The selection of an appropriate control probe is dependent on the sample probe initially selected and its expression pattern which is under investigation. The control probes may also be classified into the following three categories: (a) normalization controls; (b) expression level control; and (c) mismatch controls.

Normalization controls serve to generate signals during hybridization as a control for variations in hybridization conditions, label intensity, "reading" efficiency or any other factors that may cause the signal of a specific hybridization to vary between arrays and among different regions of the same arrays. In a preferred embodiment, signals (e.g., fluorescence intensity) read from all other probes in the array are divided by the signal (e.g., fluorescence intensity) from the control probes thereby normalizing the measurements. Typically, the normalization controls comprises sequences that are perfectly complementary to their respective target sequences. Virtually any probe may serve as a normalization control. However, it is recognized that hybridization efficiency varies with base composition and probe length. Preferred normalization probes are selected to reflect the average length of the other probes present in the array. However, they can be selected to cover a range of lengths. The normalization control(s) can also be selected to reflect the base composition of the other probes in the array.

Expression level controls are probes that hybridize specifically with constitutively expressed genes in the biological sample. Expression level controls are designed to control for the overall health and metabolic activity of a cell. Examination of the covariance of an expression level control with the expression level of the target nucleic acid indicates whether measured changes or variations in expression level of a gene is due to changes in transcription rate of that gene or to general variations in health of the cell. Thus, for example, when a cell is in poor health or lacking a critical metabolite the expression levels of both an active target gene and a constitutively expressed gene are expected to decrease. The converse is also true. Thus, where the expression levels of both an expression level control and the target gene appear to both decrease or to both increase, the change may be attributed to changes in the metabolic activity of the cell as a whole, not to differential expression of the target gene in question. Conversely, where the expression levels of this target gene and the expression level control do not covary, the variation in the expression level of the target gene is attributed to differences in regulation of that gene and not to overall variations in the metabolic activity of the cell.

Any constitutively expressed gene provides a suitable candidate for expression level control probes. Typically expression level control probes have sequences complementary to constitutively expressed "housekeeping genes," which include, but are not limited to the β-actin gene, the transferrin receptor gene, the GAPDH gene, and the like.

Mismatch probes provide a control for non-specific binding or cross-hybridization to a nucleic acid in the sample other than the target to which the probe is directed. Mismatch probes thus indicate whether a hybridization is specific or not. For example, if the target is present the perfect match probes should be consistently brighter than the mismatch probes. Typically, mismatch controls are polynucleotide probes identical to their corresponding target polynucleotide except for the presence of one or more mismatched bases. Mismatches are selected such that under appropriate hybridization conditions (e.g., stringent conditions) the test or control probe would be expected to hybridize with its target sequence, but the mismatch probe would not hybridize (or would hybridize to a significantly lesser extent). In general, as much as 20% base-pair mismatch (when optimally aligned) can be tolerated.

Control probes of any kind can be localized at any position in the array or at multiple positions throughout the array to control for spatial variation, overall expression level, or non-specific binding in hybridization assays.

The polynucleotide probes embodied in this invention can be obtained by chemical synthesis, recombinant cloning, e.g. PCR, or any combination thereof. Methods of chemical polynucleotide synthesis are well known in the art and need not be described in detail herein. One of skill in the art can use the sequence data provided herein to obtain a desired polynucleotide by employing a DNA synthesizer, PCR machine, or ordering from a commercial service.

Immobilization of Probes:

Selected probes are immobilized onto predetermined regions of a solid support by any suitable techniques that effect in stable association of the probes with the surface of a solid support. By "stably associated" is meant that the polynucleotides remain localized to the predetermined region under hybridization and washing conditions. As such, the polynucleotides can be covalently associated with or non-covalently attached to the support surface. Examples of non-covalent association include binding as a result of non-specific adsorption, ionic, hydrophobic, or hydrogen bonding interactions. Covalent association involves formation of chemical bond between the polynucleotides and a functional group present on the surface of a support. The functional may be naturally occurring or introduced as a linker. Non-limiting functional groups include but are not limited to hydroxyl, amine, thiol and amide. Exemplary techniques applicable for covalent immobilization of polynucleotide probes include, but are not limited to, UV cross-linking or other light-directed chemical coupling, and mechanically directed coupling (see, e.g. U.S. Pat. Nos. 5,837,832, 5,143,854, 5,800,992, WO 92/10092, WO 93/09668, and WO 97/10365). A preferred method is to link one of the termini of a polynucleotide probe to the support surface via a single covalent bond. Such configuration permits high hybridization efficiencies as the probes have a greater degree of freedom and are available for complex interactions with complementary targets.

Typically, each array is generated by depositing a plurality of probe samples either manually or more commonly using an automated device, which spots samples onto a number of predefined regions in a serial operation. A variety of automated spotting devices are commonly employed for production of polynucleotide arrays. Such devices include piezo or ink-jet devices, automated micro-pipetters and any of those devices that are commercially available (e.g. Beckman Biomek 2000). The total number of probe samples spotted on the support will vary depending on the number of different polynucleotide probes one wish to display on the surface, as well as the number of control probes, which may be desirable depending on the particular application in which the subject array is to be employed. Generally, the array comprises at least about 20 distinct polynucleotides, usually at least about 100 polynucleotides, preferably about 1000 polynucleotides, more preferably about 10,000 polynucleotides, but will usually not exceed 100,000 polynucleotides, wherein each polynucleotide is complementary to a distinct gene transcript. The polynucleotide spots may take a variety of configurations ranging from simple to complex, depending on the intended use of the array. The probes may be spotted in any convenient pattern across or over the surface of the array so as to from a grid, a circular, ellipsoid, oval or some other analogously curved shape.

Within a predetermined region, the probes are deposited in an amount sufficient to provided adequate hybridization and detection of target nucleic acids during a hybridization assay. Preferably, a predetermined region comprises at least 2, preferably at least 100 single-stranded polynucleotides, more preferably about 1000 single-stranded polynucleotides, and will usually not exceed 10,000 polynucleotide probes, that are complementary to the same gene transcript. Typically, a predetermined region is spotted with at least 2, usually at least 100 single-stranded polynucleotides of identical sequences. The predetermined region generally has an average size ranging from about $0.01$ cm$^2$ to about $1$ cm$^2$.

Selection of Support Substrates:

The substrates of the subject arrays may be manufactured from a variety of materials. In general, the materials with which the support is fabricated exhibit a low level of non-specific binding during hybridization assay. A preferred solid support is made from one or more of the following types of materials: nitrocellulose, nylon, polypropylene, glass, and silicon. The materials may be flexible or rigid. A flexible substrate is capable of being bent, folded, twisted or similarly manipulated, without breaking. A rigid substrate is one that is stiff or inflexible and prone to breakage. As such, the rigid substrates of the subject arrays are sufficient to provide physical support and structure to the polymeric targets present thereon under the assay conditions in which the arrays are employed, particularly under high throughput assay conditions. Exemplary materials suitable for fabricating flexible support include a diversity of membranous materials, such as nitrocellulose, nylon or derivatives thereof, and plastics (e.g. polytetrafluoroethylene, polypropylene, polystyrene, polycarbonate, and blends thereof). Examples of materials suitable for making rigid support include but are not limited to glass, semi-conductors such as silicon and germanium, metals such as platinum and gold.

The solid support on which arrays of polynucleotide probes are attached comprises at least one surface, which may be smooth or substantially planar, or with irregularities such as depressions or elevations. The surface on which the pattern of probes is deposited may be modified with one or more different layers of compounds that serve to modify the properties of the surface in a desirable manner. Modification layers coated on the solid support may comprise inorganic layers made of, e.g. metals, metal oxides, or organic layers composed of polymers or small organic molecules and the like. Polymeric layers of interest include layers of peptides, proteins, polysaccharides, lipids, phospholipids, polyurethanes, polyesters, polycarbonates, polyureas, polyamides, polyethyleneamines, polyarylene sulfates, polysiloxanes, polyimides, polyacetates and the like, where the polymers may be hetero- or homopolymeric, and may or may not be conjugated to functional moieties.

Uses of the Arrays of the Present Invention

The arrays of polynucleotide probes provide an effective means of detecting or monitoring expression of a multiplicity of genes. The expression detecting methods of this invention may be used in a wide variety of circumstances including detection of disease, identification and quantification of differential gene expression between at least two samples, linking the differentially expressed genes to a specific chromosomal location, and/or screening for compositions that upregulate or downregulate the expression or alter the pattern of expression of particular genes.

Simultaneous Detection of Multiple Gene Transcripts:

In one embodiment, this invention provides a method of simultaneously detecting expression of a multiplicity of gene transcripts of a subject. The method comprises the steps of: (a) contacting more than one labeled target polynucleotides corresponding to gene transcripts of the test subject with an array of polynucleotide probes of the invention under the conditions sufficient to produce stable target-probe complexes; and (b) detecting the formation of the stable target-probe complexes, thereby detecting expression of a multiplicity of gene transcripts.

In another embodiment, the invention provides a method for detecting differential expression of a multiplicity of gene transcripts of at least two subjects. The method involves (a) contacting more than one labeled target polynucleotides corresponding to gene transcripts of a first subject with an array of polynucleotide probes of the invention, under the conditions sufficient to produce stable target-probe complexes that form a first hybridization pattern; (b) contacting more than one labeled target polynucleotides corresponding to gene transcripts of a second subject with an invention array, under the conditions sufficient to produce stable target-probe complexes that form a second hybridization pattern; and (c) comparing the hybridization patterns, thereby detecting the differential expression of a multiplicity of gene transcripts of the subjects.

The test subject used for this invention can be body fluid, solid tissue samples, tissue cultures or cells derived therefrom and the progeny thereof, and sections or smears prepared from any of these sources, or any other samples that contain nucleic acids. As used herein, polynucleotides corresponding to gene transcripts refer to nucleic acids for whose synthesis, the mRNA transcript or subsequences thereof have ultimately served as a template. Thus, a cDNA reverse transcribed from a mRNA, an RNA molecule transcribed from that cDNA, a DNA molecule amplified from the cDNA, an RNA transcribed from the amplified DNA and etc., are all corresponding to a gene transcript.

Preparation of the target polynucleotides from the test subject can be carried out according to standard methods in the art or procedures exemplified herein (Example 3).

Briefly, DNA and RNA can be isolated using various lytic enzymes or chemical solutions according to the procedures set forth in Sambrook et al. ("Molecular Cloning: A Laboratory Manual", Second Edition,1989), or extracted by nucleic acid binding resins following the accompanying instructions provided by manufactures. Typically, target polynucleotides representing cellular mRNA pools of a subject are generated by reverse transcription using an oligo-dT primer. This has the virtue of producing a product from the 3' end of the gene transcript, directly complementary to immobilized probes on the arrays. A variation of this approach is to employ total RNA pools rather than mRNAs selected by oligo-dT, to maximize the amount of gene transcripts that can be obtained from a given amount of sample tissues or cells.

Where desired, the resulting transcribed nucleic acids may be amplified prior to hybridization. One of skill in the art will appreciate that whichever amplification method is used, if a quantitative result is desired, caution must be taken to use a method that maintains or controls for the relative copies of the amplified nucleic acids. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The subject array may also include probes specific to the internal standard for quantification of the amplified nucleic acid.

One preferred internal standard is a synthetic AW106 cRNA. The AW106 cRNA is combined with RNA isolated from the sample according to standard techniques known to those of skill in the art. The RNA is then reverse transcribed using a reverse transcriptase to provide cDNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications*, Innis et al., Academic Press, Inc. N.Y., (1990).

Further manipulation of the target polynucleotides may involve cloning the sequences into suitable vectors for replication and storage purpose. A vast number of vectors are available in the art and thus are not detailed herein. The target polynucleotides may also be modified prior to hybridization to the probe arrays in order to reduce sample complexity thereby decreasing background signal and improving sensitivity of the measurement using any techniques known in the art. See, for example, the procedures disclosed in WO 97/10365.

In assaying for expression of multiples genes of a subject, target polynucleotides are allowed to form stable complexes with probes on the aforementioned arrays in a hybridization reaction. It will be appreciated by one of skill in the art that where antisense RNA is used as the target nucleic acid, the polynucleotide probes provided in the array are chosen to be complementary to sequences of the antisense nucleic acids. Conversely, where the target nucleic acid pool is a pool of sense nucleic acids, the polynucleotide probes are selected to be complementary to sequences of the sense nucleic acids. Finally, where the nucleic acid pool is double stranded, the probes may be of either sense and/or antisense as the target nucleic acids include both sense and antisense strands.

Suitable hybridization conditions. for the practice of the present invention are such that the recognition interaction between the probe and target is both sufficiently specific and sufficiently stable. As noted above, hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, for example, (Sambrook, et al., (1989), supra).

The conditions may often be selected to be universally equally stable independent of the specific sequences involved. This typically will make use of a reagent such as an alkylammonium buffer. See, Wood et al. (1985) "Base Composition-independent Hybridization in Tetramethylammonium Chloride: A Method for Oligonucleotide Screening of Highly Complex Gene Libraries," Proc. Natl. Acad. Sci. USA, 82:1585–1588; and Krupov et al. (1989) "An Oligonucleotide Hybridization Approach to DNA Sequencing," FEBS Letters, 256:118–122; each of which is hereby incorporated herein by reference. An alkylammonium buffer tends to-minimize differences in hybridization rate and stability due to GC content. By virtue of the fact that sequences then hybridize with approximately equal affinity and stability, there is relatively little bias in strength or kinetics of binding for particular sequences. Temperature and salt conditions along with other buffer parameters may also be selected such that the kinetics of renaturation should be essentially independent of the specific target subsequence or polynucleotide probe involved. In order to ensure this, the hybridization reactions will usually be performed in a single incubation of all arrays to be tested together exposed to the identical same target probe solution under the same conditions.

Alternatively, various arrays may be individually treated differently. Different probes may be produced, each having reagents which bind to target subsequences with substantially identical stability and kinetics of hybridization. For example, all of the high GC content probes could be synthesized on a single array which is treated accordingly. In this embodiment, the arylammonium buffers could be unnecessary. Each array is then treated in a manner such that the collection of arrays show essentially uniform binding and the hybridization data of target binding to the individual array is combined with the data from other arrays to derive the necessary subsequence binding information. Preferably, control hybridization is included to determine the stringency and kinetics of each hybridization reaction.

In general, there is a tradeoff between hybridization specificity (stringency) and signal intensity. In a preferred embodiment, washing the hybridized array prior to detecting the target-probe complexes is performed to enhance the noise-signal ratio. Typically, the hybridized array is washed at successively higher stringency solutions and signals are read between each wash. Analysis of the data sets thus produced will reveal a wash stringency above which the hybridization pattern is not appreciably altered and which provides adequate signal for the particular polynucleotide probes of interest. Parameters governing the wash stringency are generally the same as those of hybridization stringency. Other measures such as inclusion of blocking reagents (e.g. sperm DNA, detergent or other organic or inorganic substances) during hybridization can also reduce non-specific binding.

For a convenient detection of the probe-target complexes formed during the hybridization assay, the target polynucleotides are conjugated to a detectable label. Detectable labels suitable for use in the present invention include any composition detectable by spectroscopic, photochemical, biochemical, immunochemical, electrical, optical or chemical means. A wide variety of appropriate detectable labels are known in the art, which include luminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The labels may be incorporated by any of a number of means well known to those of skill in the art. In one aspect, the label is simultaneously incorporated during the amplification step in the preparation of the target polynucleotides. Thus, for example, polymerase chain reaction (PCR) with labeled primers or labeled nucleotides can provide a labeled amplification product In a separate aspect, transcription reaction, as described above, using a labeled nucleotide (e.g. fluorescein-labeled UTP and/or CTP) or a labeled primer, incorporates a detectable label into the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

The detection methods used to determine where hybridization has taken place and/or to quantify the hybridization intensity will typically depend upon the label selected above. For example, radiolabels may be detected using photographic film or phosphoimager (for detecting and quantifying $^{32}$P incorporation). Fluorescent markers may be detected and quantified using a photodetector to detect emitted light (see U.S. Pat. No. 5,143,854 for an exemplary apparatus). Enzymatic labels are typically detected by providing the enzyme with a substrate and measuring the reaction product produced by the action of the enzyme on the substrate; and finally colorimetric labels are detected by simply visualizing the colored label.

The detection method provides a positional localization of the region where hybridization has taken place. The position of the hybridized region correlates to the specific sequence of the probe, and hence the identify of the gene transcript expressed in the test subject. The detection methods also yield quantitative measurement of the level of hybridization intensity at each hybridized region, and thus a direct measurement of the level of expression of a given gene transcript. A collection of the data indicating the regions of hybridization present on an array and their respective intensities constitutes a "hybridization pattern" that is representative of a multiplicity of expressed gene transcripts of a subject. Any discrepancies detected in the hybridization patterns generated by hybridizing target polynucleotides derived from different subjects are indicative of differential expression of a multiplicity of gene transcripts of these subjects.

One of skill in the art, however, will appreciate that hybridization signals will vary in strength with efficiency of hybridization, the amount of label on the target nucleic acid and the amount of particular target nucleic acid in the sample. Typically target nucleic acids present at very low levels (e.g., <1 pmol) will show a weak signal. In evaluating the hybridization data, a threshold intensity value may be selected below which a signal is not counted as being essentially indistinguishable from background. In addition, the provision of appropriate controls permits a more detailed analysis that controls for variations in hybridization conditions, cell health, non-specific binding and the like.

In one aspect, the hybridization patterns to be compared can be generated on the same array. In such case, different patterns are distinguished by the distinct types of detectable labels. In a separate aspect, the hybridization patterns employed for the comparison are generated on different arrays, where discrepancies are indicative of a differential expression of a particular gene in the subjects being compared.

The subjects employed for the comparative hybridization analysis may be (a) cells from different organisms of the same species (e.g. cells derived from different humans); (b) cells derived from the same organism but from different tissue types including normal or disease tissues, embryonic or adult tissues; (c) cells at different points in the cell-cycle; (d) cells treated with or without external or internal stimuli. Thus, the comparative hybridization analysis using the arrays of the present invention can be employed to monitor gene expression in a wide variety of contexts. Such analysis may be extended to detecting differential expression of genes between diseased and normal tissues, among different types of tissues and cells, amongst cells at different cell-cycle points or at different developmental stages, and amongst cells that are subjected to various environmental stimuli or lead drugs.

Computer-readable Media and Systems of the Present Invention

The determination of differential expression of a multiplicity of gene transcripts can be performed utilizing a computer. Accordingly, the present invention provides a computer readable medium having recorded thereon an array of polynucleotide probes as described above. As used herein, a "computer readable medium" refers to any medium which can be read and accessed directly by a computer. Such media include, but are not limited to magnetic storage media, such as floppy discs, hard disc storage medium, and magnetic tape; optical storage media such as CD-ROM; electrical storage media such as RAM and ROM; and hybrids of these categories, such as magnetic/optical storage media. A skilled artisan can readily appreciate how any of the presently known computer readable mediums can be used to create a manufacture comprising compute readable medium having recorded thereon a array of polynucleotide probes of the present invention. Likewise, it will be clear to those of skill how additional computer readable media that may be developed also can be used to create analogous manufactures having recorded thereon the invention arrays.

The term "recorded" refers to a process for storing information on computer readable medium. A skilled artisan can readily adopt any of the presently know methods for recording information on computer readable medium to generate manufactures comprising the arrays of the present invention. A variety of data storage structures are available to a skilled artisan for creating a computer readable medium having recorded thereon an array of polynucleotide probes of this invention. The choice of the data storage structure will generally be based on the means chosen to access the stored information. In addition, a variety of data processor programs and formats can be used to store the array information of the present invention on a computer readable medium.

The array information can be represented in a word processing file including but not limited to doc., txt, wpf, and formatted in commercially-available software such as WordPerfect and MicroSoft Word, or represented in the form of an ASCII file, stored in a database application, such as DB2, Sybase, Oracle, Informix, SQL or the like. The array information can also be represented in comma delimited file, tab delimited file, space delimited file, data interchange format (DIF), quatro pro file, SAS file, SPSS file, flat file, Dbase file, all adobe acrobat files: pdf, Pdf file, document template file, filemaker pro fp3 file, or the like. A skilled artisan can readily adapt any number of data-processor structuring formats (e.g., text flex or database) in order to obtain computer readable medium having recorded thereon the probe array information of the present invention.

The computer readable medium can be incorporated as part of the computer-based system of the present invention, and can be employed for a computer-based analysis as described below.

The computer-based system of the present invention is designed to detect differential expression of a multiplicity of gene transcripts indicated by a difference in hybridization patterns on an array of polynucleotide probes. Such system comprises: (a) a data storage device comprising a reference hybridization pattern and a test hybridization pattern, wherein the reference hybridization pattern is generated by hybridizing an array of polynucleotide probes as disclosed herein, with more than one labeled target polynucleotides corresponding to gene transcripts expressed in a control; and wherein the test hybridization pattern is generated by hybridizing an array of polynucleotide probes as described above with more than one labeled target polynucleotides corresponding to gene transcripts expressed in a test subject; (b) a search device for comparing the test hybridization pattern to the reference hybridization pattern of the data storage device of step (a) to detect the differences in hybridization patterns; and (c) a retrieval device for obtaining said differences in hybridization patterns of step (b).

Generally a computer-based system includes hardware and software. The "data storage device" as part of the system refers to memory which can store reference hybridization pattern(s) and test hybridization pattern(s), which are generated by hybridizing one or more arrays of polynucleotide probes as disclosed herein, with target polynucleotides corresponding to gene transcripts expressed in distinct subjects. The data-storage device may also include a memory access device which can access manufactures having recorded thereon the array information of the present invention. Non-limiting exemplary data storage devices are media storage, floppy drive, super floppy, tape drive, zip drive, syquest syjet drive, hard drive, CD Rom recordable (R), CD Rom rewritable (RW), M.D. drives, optical media, and punch cards/tape.

The "search device" as part of the computer-based system encompasses one or more programs which are implemented on the system to compare the test hybridization pattern to the reference hybridization pattern in order to detect the differences in these hybridization patterns. A variety of known algorithms are disclosed publicly and a variety of commercially available software useful for pattern recognition can be used in computer-based systems of the present invention. Examples of array analysis software include Biodiscovery, HP, and any of those applicable for image analyses. Some currently employed search devices include those embodied in "Gene Array Scanner (Hewlett Packard)", "General Scanning", "reader Hitachi system", "Genomics Solutions" and "GeneChip work station". Finally, the retrieval device includes program(s) which are implemented on the system to retrieve the differences in hybridization patterns detected by the search device. Hardware necessary for displaying the detected device may also form part of the retrieval device. The storage, search, retrieval devices may be assemble as a PC, Mac, Apollo workstation (Cray), SGI machine, Sun machine, UNIX or LINUX based Workstations, Be OS systems, laptop computer, palmtop computer, and palm pilot system, or the like.

Further provided by the present invention is a method for determining differential expression of a multiplicity of gene transcripts of at least two subjects using a computer. The computer-based method comprises the following steps: (a) providing a database comprising hybridization patterns that represent expression patterns of multiple genes for a plurality of subjects, wherein each hybridization pattern is generated by hybridizing an array of polynucleotide probes disclosed herein, with more than one labeled target polynucleotides corresponding to gene transcripts expressed in a distinct subject, wherein said hybridizing step yields detectable target-probe complexes with different levels of hybridization intensities; (b) receiving two or more of hybridization patterns for comparison; (c) determining differences in the selected hybridization patterns; and (d) displaying the results of said determination. The determining step includes the step of calculating the differences between the hybridization intensities of target-probe complexes localized in predetermined regions on the solid support.

Kits Comprising the Arrays of the Present Invention

The present invention also encompasses kits containing the polynucleotide probe arrays of this invention. Kits embodied by this invention include those that allow simultaneous detection of the expression and/or quantification of the level of expression of multiple gene transcripts of a subject. Further embodied by the invention are kits useful for detecting differential expression of a multiplicity of gene transcripts of a test subject in comparison to a control.

Each kit necessarily comprises the reagents which render the hybridization procedure possible: an array of polynucleotide probes of the invention used for detecting target polynucleotides; hybridization reagents that allow formation of stable target-probe complexes during a hybridization reaction. The kits may also contain reagents useful for generating labeled target polynucleotides corresponding to gene transcripts of a test subject. Optionally, the arrays contained in the kits may be pre-hybridized with polynucleotides corresponding to gene transcripts of the control to which the test subject is compare.

Each reagent can be supplied in a solid form or dissolved/suspended in a liquid buffer suitable for inventory storage, and later for exchange or addition into the reaction medium when the test is performed. Suitable packaging is provided. The kit can optionally provide additional components that are useful in the procedure. These optional components include, but are not limited to, buffers, capture reagents, developing reagents, labels, reacting surfaces, means for detection, control samples, instructions, and interpretive information. The kits can be employed to test a variety of biological samples, including body fluid, solid tissue samples, tissue cultures or cells derived therefrom and the progeny thereof, and sections or smears prepared from any of these sources. Diagnostic or prognostic procedures using the kits of this invention can be performed by clinical laboratories, experimental laboratories, practitioners, or private individuals.

Further illustration of the development and use of arrays and assays according to this invention are provided in the Example section below. The examples are provided as a guide to a practitioner of ordinary skill in the art, and are not meant to be limiting in any way.

EXAMPLES

Example 1

Generation of Probes

Sequence-tagged site (STS) probes (hereinafter STS tags) are generated by amplifying human genomic DNA using selected primer pairs. The selected primer pairs yield amplified sequences corresponding to the 3' untranslated region of gene transcripts of particular interest. A list of exemplary primer pairs and the resultant gene sequences are summarized in Table 1. Additional primer pairs may be obtained from worldwide web at http://www. followed by ncbi.nlm.nih.gov/dbSTS/index.html or related web sites. Each PCR reaction contains approximately 100 pmoles of each primer, 50 ng human genomic DNA, and other reagents included in Advantage Genomic PCR kit (Clontech). The PCR reaction is carried out according to manufacturer's instructions which yields approximately 5 ug of each STS tag. The resultant STS tags are analyzed, sequenced, purified, and concentrated by lyophilization (Savant) to approximately 2 ug/ul. Samples of concentrated STS tags are aliquoted and stored at low temperature for future use.

TABLE 1

STS Tags and Exemplary Primer Pairs

| Gene | STS name | STS acc # | | SEQ ID NO: | Map Position |
|---|---|---|---|---|---|
| 1. Glucokinase regulator (GCKR) | SHGC 35430 | G 29810 | Forward Primer: AACCCATGTTTCTGGGTGG<br>Reverse Primer: CGGTGAGAGTAGAAACCACTAGG | 1<br>2 | 2p23 |
| 2. Interleukin receptor, type II precursor | WI 11083 | G22557 | Forward Primer: TTTCATTTATTTCACTTGGGATAGG<br>Reverse Primer: CTTGGTTTTGGGGGGAATAT | 3<br>4 | 2q12 |
| 3. Inteleukin1 receptor, type I precursor | SHGC 35324 | G28576 | Forward Primer: GCCAAGAGTTCTTTAGGTGCC<br>Reverse Primer: TTTTTAAAAGATCTTCCCAAGCC | 5<br>6 | 2q12 |
| 4. Human insulin-like growth factor binding protein-5 (IGFBP5) | SHGC 11498 | G14572 | Forward Primer: GAATTAAATGAGGGCTGAAACG<br>Reverse Primer: CATGTGCATATTTCATTCCCC | 7<br>8 | 2q33-q36 |
| 5. Protein phosphatase 1, catalytic subunit, beta isoform (PPP1CB) | WI 7312 | G06545 | Forward Primer: ATGTGATTATGTGGTACCTTGGC<br>Reverse Primer: AATCGTATACAACATTCACATGGC | 9<br>10 | 2q22-q23 |
| 6. Human protein tyrosine phosphatase | WI 9369 | G07262 | Forward Primer: TGGACATTTCATACCTGTGCA<br>Reverse Primer: ACCTACCCTGAGGTCCGTCT | 11<br>12 | 10q25 |
| 7. Hexokinase-1 (HK1) | SHGC 11749 | G14649 | Forward Primer: TTTCCTTTATTTGGAAAAGTCAGC<br>Reverse Primer: TGCTAACCCCGTCTGCTC | 13<br>14 | 10q22 |
| 8. Arachidonate 5-lipoxygenase (ALOX5) | WI 9162 | G07156 | Forward Primer: TTCCATTTATTCTTTGATCTTCAGG<br>Reverse Primer: GCTGGGTGTGGACAGGAC | 15<br>16 | 10q11.2 |
| 9. Protein tyrosine phosphatase 2C | SHGC 30316 | G27080 | Forward Primer: CTAGAAGACAGCAGTGACACTTCC<br>Reverse Primer: TGGGGTAGTTTGGCTGCC | 17<br>18 | 12q24.21 |
| 10. Placental protein II precursor | SHGC 9798 | G11327 | Forward Primer: GGAGAGGGACTGGAAGGGATC<br>Reverse Primer: TGCCAAAATTCTAGAGGATAAAGG | 19<br>20 | 12q13.1 |
| 11. Insulin like growth factor 1 (somatomedin C) (IGF1) | WI 7033 | G06363 | Forward Primer: ACAGGAGGATTAAACAGACAGAGG<br>Reverse Primer: TTATTTAATTGTGTTTTAGAGGGCA | 21<br>22 | 12q22-q23 |
| 12. Human protein tyrosine kinase | WI 9296 | G07226 | Forward Primer: TGCTGCATAAATCACTTATCGG<br>Reverse Primer: GAACACAAATTTCTGAAAGGTGC | 23<br>24 | 12q12 |
| 13. Glycogen synthase (human liver) | WI 7963 | 006781 | Forward Primer: CATGTGCTGCATGAAGAGCT<br>Reverse Primer: AAGCTGCATAAATAGTAAGCAAAGG | 25<br>26 | 12p12.2 |
| 14. Protein tyrosine phosphatase | SHGC 31640 | G27089 | Forward Primer: TAATCAAATTACCCACCCAAGG<br>Reverse Primer: GCCTTAGGCTGTGTGATAAACC | 27<br>28 | 12q15 |
| 15. Mannose receptor (M6PR) | WI 7191 | G06444 | Forward Primer: ATAATTGCTTGTTTTCTAGCCTGG<br>Reverse Primer: TAATTGGAGTGGAAATAAAAACTGG | 29<br>30 | 10p13 |
| 16. Glutathione S-transferase, microsomal | WI 7728 | G06674 | Forward Primer: ACAACTCAACATCCAGTTGGC<br>Reverse Primer: TTCATGTCTGTTTCAGCAGTATTG | 31<br>32 | 12p12.3-p12.1 |
| 17. Glucose transporter type 3, brain | SHGC 31620 | G27088 | Forward Primer: CAGGATGAACCCAGGACG<br>Reverse Primer: GGCAAAGTTGTCATGTGCC | 33<br>34 | 12p13.3 |
| 18. Protein phosphatase 4 (formerly x) catalytic subunit (PPP4C) | WI 9235 | G07192 | Forward Primer: TTCCTCAGACGGAGGCTG<br>Reverse Primer: GGAACATGGAGCTAGGTCTCC | 35<br>36 | 16p12-16p11 |
| 19. Low density lipoprotein receptor precursor | SHGC 15376 | G15092 | Forward Primer: GTTTAAAAAGTGACACCCATCTCC<br>Reverse Primer: TGCCTCTGAAATGCCTCTTC | 37<br>38 | 19p13.3 |
| 20. Lecithin cholesterol acyltransferase | WI 10276 | G11801 | Forward Primer: TTATTGGTGGTGTCTGATGAGC<br>Reverse Primer: GGCTTCATCTCTCTTGGGG | 39<br>40 | 16q22.1 |
| 21. Interleukin 4 receptor (IL4R) | WI 9023 | G07084 | Forward Primer: AAAACTGAGGCCCTTGGG<br>Reverse Primer: ATGCCTTGGGCAGTTACAAC | 41<br>42 | 16p11.2-12.1 |
| 22. Regenerating islet-derived-1 alpha (pancreatic stone protein, pancreatic thread protein) (REG1A) | WI 9197 | G07172 | Forward Primer: CATCTCTCCAACTCAACTCAACC<br>Reverse Primer: TTTAGGGTTCCAAAGACTGGG | 43<br>44 | 2p12 |
| 23. Interleukin1, beta (IL1B) | WI 7848 | G05863 | Forward Primer: TTCTGAAAATATAACCAGCCATTG<br>Reverse Primer: ACCATTTCACATTTATTTTGAAAGC | 45<br>46 | 9q31 |
| 24. Insulin like growth factor binding protein 5 (IGFBP5) | SHGC 11498 | G14572 | Forward Primer: GAATTAAATGAGGGCTGAAACG<br>Reverse Primer: CATGTGCATATTTCATTCCCC | 47<br>48 | 2q33-q36 |

TABLE 1-continued

STS Tags and Exemplary Primer Pairs

| Gene | STS name | STS acc # | | SEQ ID NO: | Map Position |
|---|---|---|---|---|---|
| 25. Insulin receptor substrate-1 (human skeletal muscle) | WI 9260 | G07206 | Forward Primer: GTGACACCAGAATAATGAGTCTGC<br>Reverse Primer: AACCCATTCTCTCATGACACG | 49<br>50 | 2q36 |
| 26. Alkaline phosphatase, placental (Regan isozyme) (ALPP) | WI 8964 | G07054 | Forward Primer: AGTCATGGCAGCACCTGAG<br>Reverse Primer: ACCACAGCAGCCTCCTTG | 51<br>52 | 2q37 |
| 27. Human DNA dependent protein kinase catalytic subunit (DNA-PKCs) | SHGC 35517 | G29848 | Forward Primer: CTTGGTTGGCAGCATTCC | 53 | 8q11 |
| | | | Reverse Primer: TGACTTAATACTTTGGTAAGCCTGG | 54 | |
| 28. Lipoprotein lipase (LPL) | WI 9031 | 007089 | Forward Primer: TTACAAAACATACCCAGTGTTTGG<br>Reverse Primer: CTTTTTAGTGCTTGAGACTGTCTCC | 55<br>56 | 8p22 |
| 29. Human MAP kinase phosphatase (MKP-2) | SHGC 35388 | G28599 | Forward Primer: GCAGAAAGTTGGGACTGAGC<br>Reverse Primer: TGAAACTGACACATAAACCAAACC | 57<br>58 | 8p12-p11 |
| 30. Protein Kinase C, theta type | SHGC 9690 | G11293 | Forward Primer: CCCCATGTGACTTTATCTGTAGC<br>Reverse Primer: AGTCTTGAGACGTCTGTACTCCG | 59<br>60 | 10p15 |
| 31. Insulin degrading enzyme | UTR 9770 | G13262 | Forward Primer: ATTCCTGAGTCTTCCAGAGCC<br>Reverse Primer: ATGACATTTGACAATTTTTTGTTTG | 61<br>62 | 10q23-q25 |
| 32. Phosphofructokinase, muscle (PFKM) | WI 7025 | G06359 | Forward Primer: TCCACATCTTCTCAGTGTTTTAGC<br>Reverse Primer: TCACAGTGACCAGTTGGCAT | 63<br>64 | 12q13.3 |
| 33. ATP synthase lipid binding protein P2 precursor | SHGC 10801 | G13455 | Forward Primer: CCCGTGTGTTCCTTTTCCTA<br>Reverse Primer: AGGCACTCAGCCAACTGTG | 65<br>66 | 12q13.13 |
| 34. Mevalonate kinase | A001U02 | G19646 | Forward Primer: GTACAGATCGGAAGAAAGT<br>Reverse Primer: CCTTCCCTTCTACCTAAC | 67<br>68 | 12 |

Example 2

Immobilization of Probes

Approximately 5 ng of each STS tag is printed using a robot (Molecular Devices or Genomic Micro Systems) onto positively charged nylon membrane (Hybond-N+from Amersham Pharmacia Biotech). Approximately 5000 STS tags are spotted on each membrane (5cm×7cm). Each spot of sample has a diameter of about 0.1 mm, and is spaced about 0.15 mm apart. The array optionally is spotted with control samples comprising human genomic DNAs or cDNAs of house-keeping genes. The spotted STS tags and control probes are then denatured in about 0.2 M NaOH. After neutralization, the denatured probes are cross-linked to the nylon membrane by UV irradiation.

Example 3

Generation of Target Polynucleotides cDNA probes are generated by reverse transcription of mRNAs extracted from about $10 \times 10^7$ cells. Preferably, the cells are eukaryotic cells, more preferably they are mammalian cells, and even more preferably they are human cells. Total RNA molecules are isolated using NucleoSpin RNA kit (Clontech), and polyA+-RNA molecules are extracted from total RNA using mRNA Separator kit (Clontech). Labeling the target sequences is carried out during reverse transcription of the isolated RNA molecules using kits provided by Life Technology/BRL according to the following experimental procedures. The target sequences are labeled with biotin-16-biotin.

Approximately 200 ng of mRNA molecules are suspended in 16 ul water and mixed with 2 ul Oligo-dT primer (1 ug/ul 10–20 mer mixture). The reaction mixture is then denatured at about 70° C. for approximately 10 min followed by rapid chilling on ice for about 3 min. Appropriate amount of buffers containing reagents necessary for first strand synthesis (first strand buffer provided by BRL/Life Tech Cat#18064-014) and suitable amount of reverse transcriptase are added to the reaction mixture. The first stand buffer contains 1 ul DTT (0.1M), 1.5 ul dNTPs mixture (DATP, dCTP, dGTP at 20 mM, Pharmacia Cat#27-2035-02), 1.5 ul 0.8 mM dTTP and 0.8 mM biotin-16-dUTP. Typically, 1.5 ul reverse transcriptase (200 units/ul, Super-Script II RT from BRL/Life Tech Cat #18064-014) is used. The reaction mixture is then incubated at about 37° C. for approximately 90 min. The labeled target sequences are purified by passing through a Bio-Spin Chromatography Column (Bio-Rad Cat. #732-60020. Prior to hybridization with the probes immobilized on an array, the target sequences are denatured by heating at 100° C. for about 3 min followed by rapid chilling to about 4° C. For dual-color detection, 200 ng of mRNA is also reverse-transcribed in a similar labeling reaction mixture as described above which contains digoxigenin-11-dUTP instead of biotin-16-dUTP.

Example 4

Hybridization and Detection of Target-Probe Complexes Present on the Array

The array containing immobilized probes may be prehybridized for at least about 2 hours at 42° C. in a hybridization buffer (MicroHyb solution, Research Genetics, Cat #HYB125.GF) that contains 0.5 ug/ml poly- dA (Research Genetics Cat.#POLYA.GF) and 0.5 ug/ml human Cotl DNA (BRL/Life Tech Cat # 15279-011). The labeled target sequences as described above are then added to the prehybridization mixture, and incubated at about 42° C. for approximately 12–18 hours. Unbound target sequences are washed off from the array according to the following procedures: two times at 50° C. in 2×SSC, 1% SDS for 20 min and three times at room temperature in 0.2×SSC, 0.1% SDS for 15 min each. The array is then blocked in 1×BM blocking reagent (BRL/Life Tech, Cat #) for about 30 min at room temperature.

For colorimetric detection, anti-DIG-alkaline phosphatase conjugates are first diluted 15,000 fold in blocking buffer (0.1 M maleic acid, 0.15 M NaCl, and 0.3% Tween 20 at pH 7.5) containing 0.5×BM blocking reagent and incubated with the membranes at room temperature for 45 min. The membrane is then washed with blocking buffer thrice, 10 min each time. The membrane is then blocked with 1% BM blocking reagent containing 2% dextran sulphate at room temperature for 1 hour and then rinsed with 1×TBS buffer solution (10 mM Tris-HCl, pH 7.4 and 150 mM NaCl) containing 0.3% BSA. To detect the hybridized target-probe complexes on the array, streptavidin/b-galactosidase enzyme conjugate and anti-digoxigenin/alkaline phosphatase antibody-enzyme conjugate are used. The detection can also be carried out in single color mode. In this case, either one of the antibody/enzyme conjugates is used. For example, the array is typically incubated with a mixture containing 700×diluted streptavidin/b-galactosidase (GIBCO-BRL), 10,000×diluted anti-DIG-AP (Boehringer Mannheim), 4% polyethylene glycol 8000 (Sigma), and 0.3% BSA in 1×TBS buffer for 2 hours. The chromogens are generated by first treating the membrane with X-gal solution (1.2 mM X-gal, 1 mM MgCl2, 3 mM K3Fe(CN)6, 3 mM K4Fe(CN)6 in 1×TBS buffer) for 45 min at 37 C. The membrane is then rinsed briefly with deionized water and stained with Fast Red TR/Naphthol AS-MX substrate (Sigma), an alkaline phosphatase substrate. The color development reactions is then stopped by 1×PBS containing 20 mM EDTA. Target sequences labeled with biotin reacts with Strep-GAL and yields "blue" chromogen. Target sequences labeled with digoxigenin reacts with anti-Dig/AP and fast red to yield "red" chromogen.

To determine the hybridization patterns presented on the arrays, a digital camera (DCS420, Kodak) attached to a stereomicroscope (Zeiss, Stemi 2000C) is employed to scan the color images of the array. The data recorded by the digital camera can be further processed by a computer using appropriate software. For the dual-color detection system, a purple spot on the array indicates the presence of a gene commonly expressed in two separate mRNA samples derived from two separate sources. A spot exhibiting blue or red color above the average stain intensity indicates the presence of a preferentially expressed gene.

What is claimed is:

1. An array comprising a plurality of polynucleotide probes immobilized on a solid support, wherein:
   (a) the plurality of polynucleotide probes corresponds to a multiplicity of gene transcripts and comprises at least 100 polynucleotides that are each complementary to a distinct gene transcript;
   (b) each polynucleotide probe of the plurality is localized to a predetermined region on the solid support;
   (c) each polynucleotide probe of the plurality is from about 50 to 500 nucleotides in length;
   (d) each polynucleotide probe of the plurality is complementary to 3' untranslated sequence of a gene transcript, the untranslated sequence having a defined chromosomal location; and
   (e) each polynucleotide probe of the plurality is prepared by amplification of genomic DNA or cDNA using a primer pair selected from the group consisting of SEQ ID NOs. 1–2, 3–4, 5–6, 7–8, 9–10, 11–12, 13–14, 15–16, 17–18, 19–20, 21–22, 23–24, 25–26, 27–28, 29–30, 31–32, 33–34, 35–36, 37–38, 39–40, 41–42, 43–44, 45–46, 47–48, 49–50, 51–52, 53–54, 55–56, 57–58, 59–60, 61–62, 63–64, 65–66, and 67–68.

2. An array of claim 1, wherein each polynucleotide probe of the plurality of polynucleotide probes is from about 50 to 400 nucleotides in length.

3. An array of claim 1, wherein each polynucleotide probe of the plurality of polynucleotide probes is from about 50 to 300 nucleotides in length.

4. An array of claim 1, wherein the predetermined region comprises at least 2 single-stranded polynucleotides that are complementary to the same gene transcript.

5. An array of claim 1, wherein the predetermined region comprises at least 100 single-stranded polynucleotides that are complementary to the same gene transcript.

6. An array of claim 1, wherein the predetermined region comprises at least 2 single-stranded polynucleotides of identical sequences.

7. An array of claim 1, wherein the predetermined region comprises at least 100 single-stranded polynucleotides of identical sequences.

8. An array of claim 1, wherein the predetermined region has an average size ranging from about 0.01 $cm^2$ to about 1 $cm^2$.

9. An array of claim 1, wherein the plurality of polynucleotide probes is immobilized to the solid support via a covalent linkage.

10. An array of claim 1, wherein the solid support is flexible.

11. An array of claim 1, wherein the solid support is rigid.

12. An array of claim 10, wherein the solid support is made of one or more substances selected from the group consisting of nitrocellulose, nylon, polypropylene, glass, and silicon.

13. An array of claim 11, wherein the solid support is made of one or more substances selected from the group consisting of nitrocellulose, nylon, polypropylene, glass, and silicon.

14. An array of claim 1, further comprising a control probe.

15. An array of claim 14, wherein the control probe is selected from the group consisting of normalization control probe, expression level control probe, and mismatch control probe.

16. An array of claim 14, wherein the control probe has nucleotide sequence complementary to one or more constitutively expressed genes.

17. An array of claim 1, wherein each polynucleotide probe of the plurality is prepared by amplification of genomic DNA or cDNA using a pair of primers that amplify the region corresponding to 3' untranslated sequence of a gene transcript.

18. An array of claim 1, wherein the array comprises a polynucleotide probe prepared by amplification of genomic DNA or cDNA using a primer pair selected from the group consisting of SEQ ID NOs. 1–2, 3–4, 5–6, 7–8, 9–10, 11–12, 13–14, 15–16, 17–18, 19–20, 21–22, 23–24, 25–26, 27–28, 29–30, 31–32, 33–34, 35–36, 37–38, 39–40, 41–42, 43–44, 45–46, 47–48, 49–50, 51–52, 53–54, 55–56, 57–58, 59–60, 61–62, 63–64, 65–66, and 67–68 and at least one control probe.

19. An array of claim 1 further comprising target polynucleotides corresponding to gene transcripts expressed in a subject, wherein the target polynucleotides are bound to the polynucleotide probes in form of stable target-probe hybridization complexes.

20. An array of claim 19, wherein the target polynucleotides are conjugated with a detectable label selected from the group consisting of an enzyme, a radioactive isotope and a luminescent substance.

21. An array of claim 19, wherein the target polynucleotides are DNA or RNA molecules.

22. An array of claim 19, wherein the target polynucleotides are cDNAs.

23. A method of preparing an array of polynucleotide probes corresponding to a multiplicity of gene transcripts, the method comprising:
   (a) generating a plurality of gene-specific polynucleotides by amplification of genomic DNA or cDNA using a primer pair selected from the group consisting of SEQ ID NOs. 1–2, 3–4, 5–6, 7–8, 9–10, 11–12, 13–14, 15–16, 17–18, 19–20, 21–22, 23–24, 25–26, 27–28, 29–30, 31–32, 33–34, 35–36, 37–38, 39–40, 41–42, 43–44, 45–46, 47–48, 49–50, 51–52, 53–54, 55–56, 57–58, 59–60, 61–62, 63–64, 65–66, and 67–68, wherein each polynucleotide of the plurality is from about 50 to about 500 nucleotides in length, and wherein each polynucleotide is complementary to 3' untranslated sequence of a gene transcript, the untranslated sequence having a defined chromosomal location;
   (b) immobilizing the plurality of polynucleotides in a predetermined region on a solid support; and
   (c) repeating steps (a) and (b) to yield an array of polynucleotide probes corresponding to a multiplicity of gene transcripts.

24. A method of using an array to detect gene expression in a sample, the method comprising:
   (a) contacting the polynucleotide probes of the array of claim 1 with labeled target polynucleotides from the sample under conditions to form stable target-probe complexes; and
   (b) detecting complex formation, thereby detecting gene expression in the sample.

* * * * *

SEQUENCE LISTING

```
<160> NUMBER OF SEQ ID NOS: 68

<210> SEQ ID NO 1
<211> LENGTH: 19
<212> TYPE: DNA
<213> ORGANISM: Homo Sapien

<400> SEQUENCE: 1
aacccatgtt tctgggtgg                                                 19

<210> SEQ ID NO 2
<211> LENGTH: 23
<212> TYPE: DNA
<213> ORGANISM: Homo Sapien

<400> SEQUENCE: 2
cggtgagagt agaaaccact agg                                            23

<210> SEQ ID NO 3
<211> LENGTH: 25
<212> TYPE: DNA
<213> ORGANISM: Homo Sapien

<400> SEQUENCE: 3
tttcatttat ttcacttggg atagg                                          25

<210> SEQ ID NO 4
<211> LENGTH: 20
<212> TYPE: DNA
<213> ORGANISM: Homo Sapien

<400> SEQUENCE: 4
cttggttttg gggggaatat                                                20

<210> SEQ ID NO 5
<211> LENGTH: 21
<212> TYPE: DNA
<213> ORGANISM: Homo Sapien

<400> SEQUENCE: 5
```

-continued

| | |
|---|---|
| gccaagagtt ctttaggtgc c | 21 |

<210> SEQ ID NO 6
<211> LENGTH: 23
<212> TYPE: DNA
<213> ORGANISM: Homo Sapien

<400> SEQUENCE: 6

| | |
|---|---|
| tttttaaaag atcttcccaa gcc | 23 |

<210> SEQ ID NO 7
<211> LENGTH: 22
<212> TYPE: DNA
<213> ORGANISM: Homo Sapien

<400> SEQUENCE: 7

| | |
|---|---|
| gaattaaatg agggctgaaa cg | 22 |

<210> SEQ ID NO 8
<211> LENGTH: 21
<212> TYPE: DNA
<213> ORGANISM: Homo Sapien

<400> SEQUENCE: 8

| | |
|---|---|
| catgtgcata tttcattccc c | 21 |

<210> SEQ ID NO 9
<211> LENGTH: 23
<212> TYPE: DNA
<213> ORGANISM: Homo Sapien

<400> SEQUENCE: 9

| | |
|---|---|
| atgtgattat gtggtacctt ggc | 23 |

<210> SEQ ID NO 10
<211> LENGTH: 24
<212> TYPE: DNA
<213> ORGANISM: Homo Sapien

<400> SEQUENCE: 10

| | |
|---|---|
| aatcgtatac aacattcaca tggc | 24 |

<210> SEQ ID NO 11
<211> LENGTH: 21
<212> TYPE: DNA
<213> ORGANISM: Homo Sapien

<400> SEQUENCE: 11

| | |
|---|---|
| tggacatttc atacctgtgc a | 21 |

<210> SEQ ID NO 12
<211> LENGTH: 20
<212> TYPE: DNA
<213> ORGANISM: Homo Sapien

<400> SEQUENCE: 12

| | |
|---|---|
| acctaccctg aggtccgtct | 20 |

<210> SEQ ID NO 13
<211> LENGTH: 24
<212> TYPE: DNA
<213> ORGANISM: Homo Sapien

<400> SEQUENCE: 13

```
tttcctttat ttgaaaagt cagc                                              24

<210> SEQ ID NO 14
<211> LENGTH: 18
<212> TYPE: DNA
<213> ORGANISM: Homo Sapien

<400> SEQUENCE: 14
tgctaacccc gtctgctc                                                    18

<210> SEQ ID NO 15
<211> LENGTH: 25
<212> TYPE: DNA
<213> ORGANISM: Homo Sapien

<400> SEQUENCE: 15 ttccattat tctttgatct tcagg                                             25

<210> SEQ ID NO 16
<211> LENGTH: 18
<212> TYPE: DNA
<213> ORGANISM: Homo Sapien

<400> SEQUENCE: 16
gctgggtgtg gacaggac                                                    18

<210> SEQ ID NO 17
<211> LENGTH: 24
<212> TYPE: DNA
<213> ORGANISM: Homo Sapien

<400> SEQUENCE: 17
ctagaagaca gcagtgacac ttcc                                             24

<210> SEQ ID NO 18
<211> LENGTH: 18
<212> TYPE: DNA
<213> ORGANISM: Homo Sapien

<400> SEQUENCE: 18
tggggtagtt tggctgcc                                                    18

<210> SEQ ID NO 19
<211> LENGTH: 20
<212> TYPE: DNA
<213> ORGANISM: Homo Sapien

<400> SEQUENCE: 19
ggagaggact ggaagggatc                                                  20

<210> SEQ ID NO 20
<211> LENGTH: 24
<212> TYPE: DNA
<213> ORGANISM: Homo Sapien

<400> SEQUENCE: 20
tgccaaaatt ctagaggata aagg                                             24

<210> SEQ ID NO 21
<211> LENGTH: 24
<212> TYPE: DNA
<213> ORGANISM: Homo Sapien
```

<400> SEQUENCE: 21
acaggaggat taaacagaca gagg                                      24

<210> SEQ ID NO 22
<211> LENGTH: 25
<212> TYPE: DNA
<213> ORGANISM: Homo Sapien

<400> SEQUENCE: 22
ttatttaatt gtgttttaga gggca                                     25

<210> SEQ ID NO 23
<211> LENGTH: 22
<212> TYPE: DNA
<213> ORGANISM: Homo Sapien

<400> SEQUENCE: 23
tgctgcataa atcacttatc gg                                        22

<210> SEQ ID NO 24
<211> LENGTH: 23
<212> TYPE: DNA
<213> ORGANISM: Homo Sapien

<400> SEQUENCE: 24
gaacacaaat ttctgaaagg tgc                                       23

<210> SEQ ID NO 25
<211> LENGTH: 20
<212> TYPE: DNA
<213> ORGANISM: Homo Sapien

<400> SEQUENCE: 25
catgtgctgc atgaagagct                                           20

<210> SEQ ID NO 26
<211> LENGTH: 25
<212> TYPE: DNA
<213> ORGANISM: Homo Sapien

<400> SEQUENCE: 26
aagctgcata aatagtaagc aaagg                                     25

<210> SEQ ID NO 27
<211> LENGTH: 22
<212> TYPE: DNA
<213> ORGANISM: Homo Sapien

<400> SEQUENCE: 27
taatcaaatt acccacccaa gg                                        22

<210> SEQ ID NO 28
<211> LENGTH: 22
<212> TYPE: DNA
<213> ORGANISM: Homo Sapien

<400> SEQUENCE: 28
gccttaggct gtgtgataaa cc                                        22

<210> SEQ ID NO 29
<211> LENGTH: 24
<212> TYPE: DNA
<213> ORGANISM: Homo Sapien

<400> SEQUENCE: 29
ataattgctt gttttctagc ctgg                              24

<210> SEQ ID NO 30
<211> LENGTH: 25
<212> TYPE: DNA
<213> ORGANISM: Homo Sapien

<400> SEQUENCE: 30
taattggagt ggaaataaaa actgg                             25

<210> SEQ ID NO 31
<211> LENGTH: 21
<212> TYPE: DNA
<213> ORGANISM: Homo Sapien

<400> SEQUENCE: 31
acaactcaac atccagttgg c                                 21

<210> SEQ ID NO 32
<211> LENGTH: 24
<212> TYPE: DNA
<213> ORGANISM: Homo Sapien

<400> SEQUENCE: 32
ttcatgtctg tttcagcagt attg                              24

<210> SEQ ID NO 33
<211> LENGTH: 18
<212> TYPE: DNA
<213> ORGANISM: Homo Sapien

<400> SEQUENCE: 33
caggatgaac ccaggacg                                     18

<210> SEQ ID NO 34
<211> LENGTH: 19
<212> TYPE: DNA
<213> ORGANISM: Homo Sapien

<400> SEQUENCE: 34
ggcaaagttg tcatgtgcc                                    19

<210> SEQ ID NO 35
<211> LENGTH: 18
<212> TYPE: DNA
<213> ORGANISM: Homo Sapien

<400> SEQUENCE: 35
ttcctcagac ggaggctg                                     18

<210> SEQ ID NO 36
<211> LENGTH: 21
<212> TYPE: DNA
<213> ORGANISM: Homo Sapien

<400> SEQUENCE: 36
ggaacatgga gctaggtctc c                                 21

<210> SEQ ID NO 37
<211> LENGTH: 24
<212> TYPE: DNA

```
<213> ORGANISM: Homo Sapien

<400> SEQUENCE: 37
gtttaaaaag tgacacccat ctcc                                          24

<210> SEQ ID NO 38
<211> LENGTH: 20
<212> TYPE: DNA
<213> ORGANISM: Homo Sapien

<400> SEQUENCE: 38
tgcctctgaa atgcctcttc                                               20

<210> SEQ ID NO 39
<211> LENGTH: 22
<212> TYPE: DNA
<213> ORGANISM: Homo Sapien

<400> SEQUENCE: 39
ttattggtgg tgtctgatga gc                                            22

<210> SEQ ID NO 40
<211> LENGTH: 19
<212> TYPE: DNA
<213> ORGANISM: Homo Sapien

<400> SEQUENCE: 40
ggcttcatct ctcttgggg                                                19

<210> SEQ ID NO 41
<211> LENGTH: 18
<212> TYPE: DNA
<213> ORGANISM: Homo Sapien

<400> SEQUENCE: 41
aaaactgagg cccttggg                                                 18

<210> SEQ ID NO 42
<211> LENGTH: 20
<212> TYPE: DNA
<213> ORGANISM: Homo Sapien

<400> SEQUENCE: 42
atgccttggg cagttacaac                                               20

<210> SEQ ID NO 43
<211> LENGTH: 23
<212> TYPE: DNA
<213> ORGANISM: Homo Sapien

<400> SEQUENCE: 43
catctctcca actcaactca acc                                           23

<210> SEQ ID NO 44
<211> LENGTH: 21
<212> TYPE: DNA
<213> ORGANISM: Homo Sapien

<400> SEQUENCE: 44
tttagggttc caaagactgg g                                             21

<210> SEQ ID NO 45
<211> LENGTH: 24
```

```
<212> TYPE: DNA
<213> ORGANISM: Homo Sapien

<400> SEQUENCE: 45
ttctgaaaat ataaccagcc attg                                    24

<210> SEQ ID NO 46
<211> LENGTH: 25
<212> TYPE: DNA
<213> ORGANISM: Homo Sapien

<400> SEQUENCE: 46
accatttcac atttattttg aaagc                                   25

<210> SEQ ID NO 47
<211> LENGTH: 22
<212> TYPE: DNA
<213> ORGANISM: Homo Sapien

<400> SEQUENCE: 47
gaattaaatg agggctgaaa cg                                      22

<210> SEQ ID NO 48
<211> LENGTH: 21
<212> TYPE: DNA
<213> ORGANISM: Homo Sapien

<400> SEQUENCE: 48
catgtgcata tttcattccc c                                       21

<210> SEQ ID NO 49
<211> LENGTH: 24
<212> TYPE: DNA
<213> ORGANISM: Homo Sapien

<400> SEQUENCE: 49
gtgacaccag aataatgagt ctgc                                    24

<210> SEQ ID NO 50
<211> LENGTH: 21
<212> TYPE: DNA
<213> ORGANISM: Homo Sapien

<400> SEQUENCE: 50
aacccattct ctcatgacac g                                       21

<210> SEQ ID NO 51
<211> LENGTH: 19
<212> TYPE: DNA
<213> ORGANISM: Homo Sapien

<400> SEQUENCE: 51
agtcatggca gcacctgag                                          19

<210> SEQ ID NO 52
<211> LENGTH: 18
<212> TYPE: DNA
<213> ORGANISM: Homo Sapien

<400> SEQUENCE: 52
accacagcag cctccttg                                           18

<210> SEQ ID NO 53
```

-continued

<210> SEQ ID NO 53
<211> LENGTH: 18
<212> TYPE: DNA
<213> ORGANISM: Homo Sapien

<400> SEQUENCE: 53
cttggttggc agcattcc                                                18

<210> SEQ ID NO 54
<211> LENGTH: 25
<212> TYPE: DNA
<213> ORGANISM: Homo Sapien

<400> SEQUENCE: 54
tgacttaata ctttggtaag cctgg                                        25

<210> SEQ ID NO 55
<211> LENGTH: 24
<212> TYPE: DNA
<213> ORGANISM: Homo Sapien

<400> SEQUENCE: 55
ttacaaaaca tacccagtgt ttgg                                         24

<210> SEQ ID NO 56
<211> LENGTH: 25
<212> TYPE: DNA
<213> ORGANISM: Homo Sapien

<400> SEQUENCE: 56 cttttagtg cttgagactg tctcc                                         25

<210> SEQ ID NO 57
<211> LENGTH: 20
<212> TYPE: DNA
<213> ORGANISM: Homo Sapien

<400> SEQUENCE: 57
gcagaaagtt gggactgagc                                              20

<210> SEQ ID NO 58
<211> LENGTH: 24
<212> TYPE: DNA
<213> ORGANISM: Homo Sapien

<400> SEQUENCE: 58
tgaaactgac acataaacca aacc                                         24

<210> SEQ ID NO 59
<211> LENGTH: 23
<212> TYPE: DNA
<213> ORGANISM: Homo Sapien

<400> SEQUENCE: 59
ccccatgtga ctttatctgt agc                                          23

<210> SEQ ID NO 60
<211> LENGTH: 23
<212> TYPE: DNA
<213> ORGANISM: Homo Sapien

<400> SEQUENCE: 60
agtcttgaga cgtctgtact ccg                                          23

```
<210> SEQ ID NO 61
<211> LENGTH: 21
<212> TYPE: DNA
<213> ORGANISM: Homo Sapien

<400> SEQUENCE: 61
attcctgagt cttccagagc c                                              21

<210> SEQ ID NO 62
<211> LENGTH: 25
<212> TYPE: DNA
<213> ORGANISM: Homo Sapien

<400> SEQUENCE: 62
atgacatttg acaatttttt gtttg                                          25

<210> SEQ ID NO 63
<211> LENGTH: 24
<212> TYPE: DNA
<213> ORGANISM: Homo Sapien

<400> SEQUENCE: 63
tccacatctt ctcagtgttt tagc                                           24

<210> SEQ ID NO 64
<211> LENGTH: 20
<212> TYPE: DNA
<213> ORGANISM: Homo Sapien

<400> SEQUENCE: 64
tcacagtgac cagttggcat                                                20

<210> SEQ ID NO 65
<211> LENGTH: 20
<212> TYPE: DNA
<213> ORGANISM: Homo Sapien

<400> SEQUENCE: 65
cccgtgtgtt cctttcccta                                                20

<210> SEQ ID NO 66
<211> LENGTH: 19
<212> TYPE: DNA
<213> ORGANISM: Homo Sapien

<400> SEQUENCE: 66
aggcactcag ccaactgtg                                                 19

<210> SEQ ID NO 67
<211> LENGTH: 19
<212> TYPE: DNA
<213> ORGANISM: Homo Sapien

<400> SEQUENCE: 67
gtacagatcg gaagaaagt                                                 19

<210> SEQ ID NO 68
<211> LENGTH: 18
<212> TYPE: DNA
<213> ORGANISM: Homo Sapien

<400> SEQUENCE: 68
ccttcccttc tacctaac                                                  18
```